United States Patent [19]
Dias

[11] Patent Number: 5,577,506
[45] Date of Patent: Nov. 26, 1996

[54] CATHETER PROBE HAVING A FIXED ACOUSTIC REFLECTOR FOR FULL-CIRCLE IMAGING

[75] Inventor: J. Fleming Dias, Palo Alto, Calif.

[73] Assignee: Hewlett Packard Company, Palo Alto, Calif.

[21] Appl. No.: 550,415

[22] Filed: Oct. 30, 1995

Related U.S. Application Data

[63] Continuation of Ser. No. 288,523, Aug. 10, 1994, abandoned.

[51] Int. Cl.⁶ ........................................... A61B 8/00
[52] U.S. Cl. ........................... 128/662.03; 310/366
[58] Field of Search .................. 128/661.01, 660.08, 128/662.03, 662.05, 663.01; 73/603, 620, 621, 624, 625; 310/334, 335, 336, 365, 366

[56] References Cited

U.S. PATENT DOCUMENTS

| | | | |
|---|---|---|---|
| 4,208,602 | 6/1980 | Stoller | 310/335 |
| 4,217,909 | 8/1980 | Papadofrangakis et al. | 128/661.01 |
| 4,338,821 | 7/1982 | Dion | 73/603 |
| 4,495,817 | 1/1985 | Hunt et al. | 73/624 |
| 4,508,122 | 4/1985 | Gardineer et al. | 73/620 |
| 5,273,045 | 12/1993 | Chihara et al. | 128/662.06 |
| 5,284,148 | 2/1994 | Dias et al. | 128/662.06 |
| 5,291,090 | 3/1994 | Dias | 310/334 |
| 5,291,893 | 3/1994 | Slayton | 128/662.06 |
| 5,295,484 | 3/1994 | Marcus et al. | 128/660.03 |

OTHER PUBLICATIONS

Cavaye, Douglas M. et al., "Ultravascular Ultrasound Imaging," Raven Press Ltd., New York, 1993, pp. 1–44.
O'Donnell, M. et al., "Efficient Synthetic Aperture Imaging from a Circular Aperture with Possible Application to Catheter-Based Imaging," *IEEE Transactions of Ultrasonics, Ferroelectrics, and Frequency Control*, vol. 39, No. 3, May 1992, pp. 366–380.

*Primary Examiner*—George Manuel

[57] ABSTRACT

An ultrasonic probe, such as a catheter, includes an array of electroacoustic transducer elements arranged about a central region, with each element having a radiating surface directed to define a first acoustic energy path having a component of direction that is toward the central region. That is, the elements are inwardly directed. Within the central region is an acoustic reflector that reflects the acoustic energy along a second path to an object to be imaged. In another embodiment, the transducer elements are directed to project acoustic energy generally parallel to the axis of the ultrasonic probe, with the acoustic reflector providing reflection for defining an interrogation beam.

23 Claims, 6 Drawing Sheets

CATHETER PROBE HAVING A FIXED ACOUSTIC REFLECTOR FOR FULL-CIRCLE IMAGING

CROSS REFERENCE TO RELATED APPLICATION

This is a continuation of application Ser. No. 08/288,523 filed on Aug. 10, 1994, now abandoned.

TECHNICAL FIELD

The invention relates generally to ultrasonic devices and more particularly to ultrasonic probes for imaging and/or treating the interior of a conduit, such as a human blood vessel.

BACKGROUND ART

Ultrasonic devices are used to diagnose and treat cardiovascular disorders. Ultrasonic imaging can be performed in the non-invasive manner of transmitting acoustic waves into a body of interest and detecting the resulting reflections of the waves. The reflections occur as a result of changes in acoustic impedance, so that time delays in receiving the reflections or phase changes of the reflections can be used to form images of organs or other tissue within the body of interest. However, non-invasive ultrasonic imaging has a number of limitations. For example, adequate resolution of target tissue deep within the body is limited by accessibility of the tissue to the acoustic beam and by the frequency of the beam. The target tissue may be inaccessible through the bone and/or lung structure and closer tissue of a patient. With regard to frequency, higher frequencies provide the short wavelengths that enhance resolution, but the higher frequencies attenuate more rapidly, limiting the depth of penetration.

In some applications, intracorporeal ultrasonic devices overcome these limitations. A single transducer element or an array of transducer elements within a probe can be used to transmit and receive acoustic beams when placed within the body of interest. Catheter probes provide a 360° cross-sectional image of a vessel by passing the probe through the vessel. Both mechanical and electrically switched catheters are known. U.S. Pat. No. 5,273,045 to Chihara et al. describes both types of catheters. In one embodiment of a mechanical catheter, a single piezoelectric element is directed at a 90° angle to the longitudinal axis of the catheter, and the element is caused to rotate to provide a full-circle image. In a second embodiment of a mechanical catheter, a single transducer element directs an acoustic beam along the longitudinal axis of the catheter, and a reflector is used to deflect the beam at a 90° angle to the axis. The reflector is mechanically rotated to image the entire surrounding area. Turning to electrically switched catheters, the Chihara et al. patent describes and illustrates a conventional electrically switched catheter as having an array of piezoelectric elements arranged about the circumference of a cylindrical region of a probe tip. Excitation of the piezoelectric elements is phased and sequenced to image the region surrounding the probe tip. While each of the embodiments provides transverse scanning, look-forward and look-rearward catheters can be formed with only relatively minor adaptations. Chihara et al. also describe an embodiment in which imaging is directly forward of the path of the catheter. Other intravascular devices that utilize multiple transducer elements are described in U.S. Pat. Nos. 5,284,148 to Dias et al. and 5,291,090 to Dias, which are assigned to the assignee of the present application.

For the conventional electrically switched catheter, the transducer elements along the outer surface of a cylindrical region of the catheter are selectively triggered and phase shifts are introduced in order to generate a generally planar wavefront. However, only a limited number of transducer elements can be triggered at a single time. As an example, if a 32-element catheter is employed, the 16 elements that are on the side of the catheter opposite to the direction of the wavefront must remain inactive. Of the other 16 elements, use of the elements that are at the greatest angle to the direction of the wavefront requires large phase shifts, with image-generating contributions of these elements being highly apodized because of shading effects. Thus, in practice the maximum number of elements that can be activated at a given time are only those elements within a 90° sector. If the imaging rotation is in a clockwise direction, progression takes place by electrically exciting the previously unexcited element beyond the clockwise end of the 90° sector and terminating excitation of the element at the counterclockwise end of the original 90° sector. That is, the 90° sector progressively sweeps about the transducer array by initiating excitation of a front-end element and terminating the excitation of a back-end element.

While the prior art method of forming and operating an electrically switched catheter functions well in many applications, the arrangement has some limitations. As previously noted, a relatively small fraction of the total number of transducer elements is used at one time. Moreover, the beam-forming characteristics of the circular array are significantly less than optimal. It is difficult to image structures that are in near contact to the imaging ultrasonic array. The close proximity of the array to the structure of interest increases the adverse effects of the imaging component sometimes referred to as the "ring-down artifact." This phenomenon results in poor resolution in the near field of the scan.

What is needed is an ultrasonic probe, such as a catheter, which provides high resolution full-circle imaging even in the near field.

SUMMARY OF THE INVENTION

An ultrasonic probe in accordance with the invention includes an array of electroacoustic transducer elements that are directed to define acoustic beams that converge toward a central region. In the preferred embodiment, the transducer elements are in a circular array, with the acoustic beams being directed generally at the axis. An acoustic reflector is positioned within the central region in spaced-apart relationship with the transducer elements to redirect the acoustic beams to form an interrogation beam for imaging an object beyond the radial extent of the array of transducer elements. Acoustic energy that returns by echo from the object of interest contacts the acoustic reflector and is deflected to the array. Since the acoustic beams are directed inwardly in a converging manner, a greater number of transducer elements can be excited at a given time.

The transducer elements may define a first truncated conical volume, with the transducer elements having forward surfaces that are directed to define a first acoustic energy path having a component of direction that is toward the central region. The array is typically formed on a shell having an interior surface of the desired shape. Optionally, the shell is impedance matched with the transducer elements, so that the elements may be fixed on the outer surface and formed to direct the acoustic beams through the shell to the acoustic reflector. Electrodes are electrically connected to each transducer element for electrically exciting the elements. Typically, a multiplexer circuit is used to excite selected transducer elements, with the excitation progressing about the array to form a full-circle image of the object of interest. However, excitation of a subset of the elements can be progressed mechanically by rotating a multi-element contact.

The acoustic reflector has a geometry which defines the direction of the interrogation beam and may be used to partially determine the characteristics of the interrogation beam. In one embodiment, the acoustic reflector has a frustroconical configuration. The slope of the reflector determines whether the interrogation beam will emerge in a look-forward direction, a transverse direction or a look-back direction. Other solids of revolution are possible in order to reshape the interrogation beam. For example, a reflector may have an outer surface that varies in half angle to the axis in order to provide focused interrogation and echo beams. In another embodiment, the transducer elements each project acoustic beams that are parallel to the axis of the acoustic probe. A fixed reflector redirects the beams to the object of interest. Again, a subset of elements are excited at a single time, with the subset being progressed to provide a full-circle image.

An advantage of the invention is that by converging the acoustic beams from the transducer elements before the acoustic energy is directed toward the object of interest, a greater number of transducer elements may be included in the subset of elements fired at a particular time. Thus, the image-forming capabilities of the ultrasonic probe are enhanced. Another advantage is that the acoustic energy travels a short distance before it is directed to the object of interest. Particularly if the acoustic path from the transducer elements to the reflector is inwardly directed, any adverse effects of imaging objects immediately adjacent to transducer elements are reduced. Another advantage is that the space between the elements and the reflector may be a liquid, allowing the reflector to be moved axially toward and away from the array in order to selectively translate the focus of the interrogation beam.

BEST MODE FOR CARRYING OUT THE INVENTION

Figure 1:
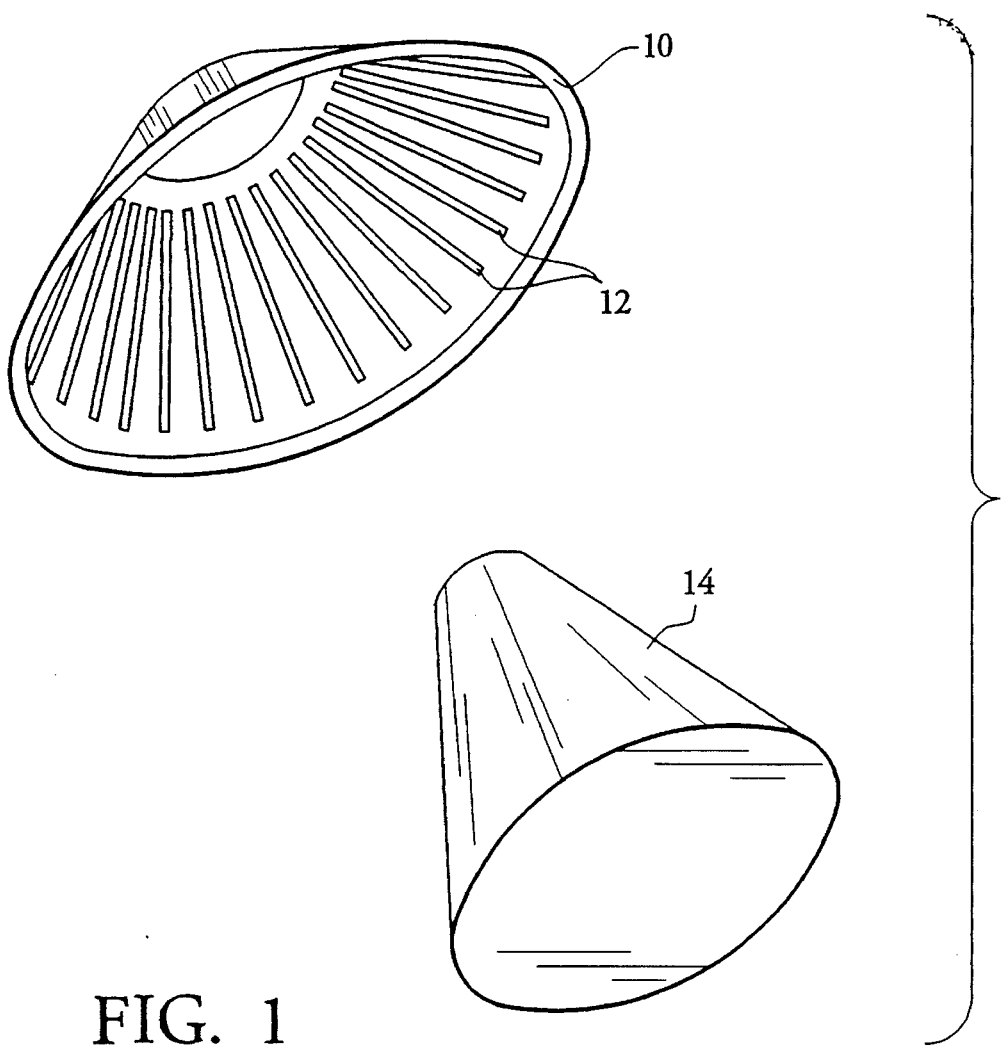
FIG. 1 is an exploded view of a transducer array and an acoustic reflector in accordance with the invention.

With reference to FIG. 1, a frustroconically-shaped shell 10 includes an array of transducer elements 12 on an interior surface of the shell. The transducer elements are evenly spaced about the interior surface. The array may include sixty-four elements, but the number of transducer elements is not important to implementing the invention. Also shown in FIG. 1 is a frustroconically shaped acoustic reflector 14. As will be explained more fully below, the reflector 14 functions as a mirror for acoustic energy generated by the transducer elements 12 and for echo energy to be received by the transducer elements.

Figure 2:
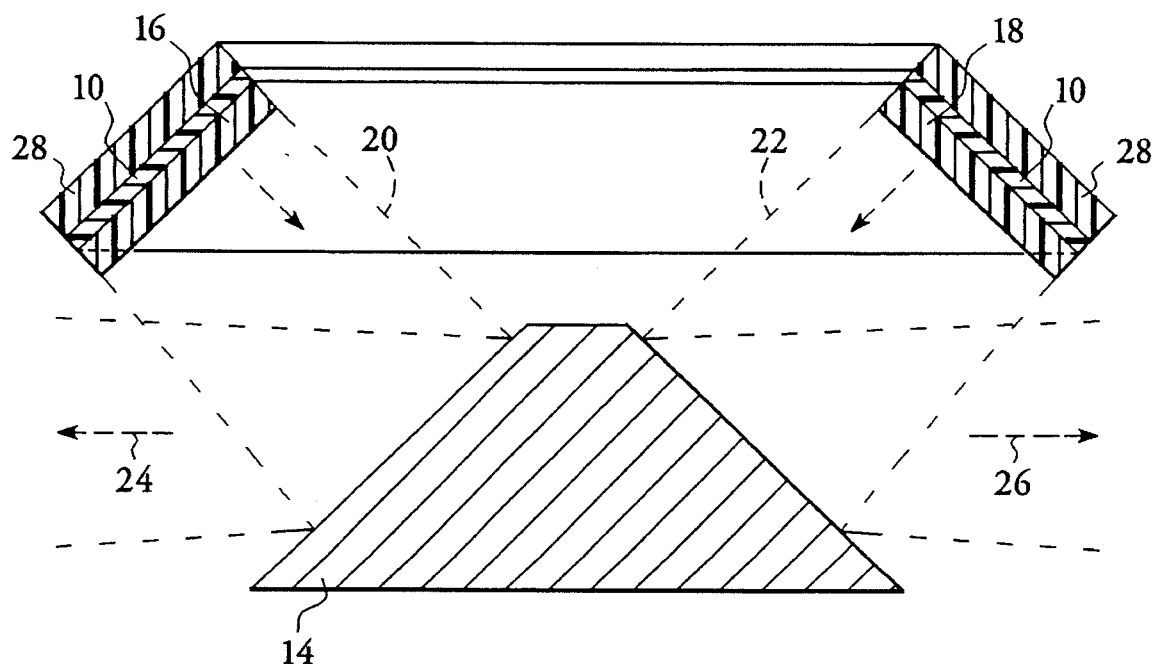
FIG. 2 is a schematic diametrical view of the reflector and two transducers of the array of FIG. 1.

Referring now to FIG. 1 and 2, a pair of transducer elements 16 and 18 on the interior surface of the shell 10 are shown as directing acoustic beams 20 and 22 toward the reflector 14. Upon reaching the reflector, the energy is redirected at an angle of 90° relative to the coincident axes of the reflector 14 and shell 10. In operation, the shell and reflector are housed within a sheath that can be inserted in an axial direction through a conduit, such as a blood vessel of a human. That is, the acoustic energy from the surface of the reflector is in a direction perpendicular to the travel of the catheter probe. However, the geometry of either or both of the shell 10 and reflector 14 can be modified to direct acoustic energy at either a look-forward or a look-back direction. For example, a decrease in the half angle of the reflector 14 will provide a look-back probe in which acoustic energy is directed rearwardly of a probe inserted toward the virtual vertices of the shell and reflector.

While FIG. 2 includes a pair of arrows 24 and 26 representing acoustic energy emitted in opposite directions. However, the array of transducer elements on the shell 10 is typically operated in the same manner as conventional electronically-switched transducer arrays, so that only a subset of elements is activated during a particular period of time, with the activation being systematically rotated about the axis of the array. For example, if the interrogation beam is to swing in a clockwise direction from the reference position 24 of FIG. 2, the inactive element immediately adjacent to the element subset for generating the interrogation beam is activated. At the same time, the element at the counter-clockwise end of the previous subset is inactivated, leaving the same number of excited transducer elements. This technique of activating a new lead element and deactivating a trail element continues in order to achieve a full-circle image of the object into which the catheter probe is inserted.

In addition to the generation of acoustic energy, the transducer elements 12, 16 and 18 are employed to receive echo energy from the object of interest. A portion of the energy of the interrogation beam is reflected back toward the reflector 14 upon encountering a change in acoustic impedance. The echo signal is then redirected to the array of transducer elements, which are capable of detecting the energy. The detected energy is then employed to create an image using known techniques.

The material for forming the transducer elements 12, 16 and 18 is not critical. For low frequency operation, e.g. 5 MHz, a suitable material may be a piezoelectric of the lead zirconate titanate series (PZT). Operation at higher frequencies, e.g. 40 MHz, is possible using zinc oxide that is deposited on the shell 10 and photolithographically patterned. Alternatives to zinc oxide are polyvinylidene difluoride (PVDF) and its copolymers. The thickness of the transducer is related to the desired operating frequency of the transducer element. The relationship between the desired frequency ($f_0$) and the thickness (t) of the transducer is $f_0 = V_L/2t$, where $V_L$ is the longitudinal velocity of the acoustic wavefront in the transducer material.

The shell 10 is formed of either an electrically conducting or insulative material. An acceptable insulative material is fused quartz coated with a chromium-gold film that functions as an electrode layer. If the shell is formed of a conductive material, the shell may be used as a common electrode for operating the transducer elements 12, 16 and 18. On the surface of the shell opposite to the transducer elements 12, 16 and 18 is a layer 28 of material for absorbing rearwardly directed acoustic energy, in order to decrease the pulse width, and consequently the in-line resolution capabilities of the ultrasonic probe.

Not shown in FIG. 2 are electrodes for exciting the transducer elements 16 and 18. A single electrode may be universally connected to the elements of the transducer array at the rearward element surfaces, i.e., between the shell 10 and the transducer elements 16 and 18. Individual electrodes are then formed on the forward element surfaces. An acceptable metallization for the electrodes is a 2000 Å gold layer atop a 100 Å chromium layer. Conventional wiring and multiplexing techniques can then be utilized to selectively trigger subsets of elements of the transducer array, using on-board integrated circuits.

While not shown in FIG. 2, an impedance matching layer is typically formed on the forward surfaces of the transducer elements 16 and 18. The impedance matching layer improves the efficiency of transmitting acoustic energy by providing a gradual transition between the impedance of the piezoelectric material of the elements and the coupling fluid within the catheter probe. The coupling fluid is selected to provide an impedance match with the medium surrounding the catheter probe. For intravascular examination, an acceptable coupling fluid is a saline solution, which can include additives that maintain a sterile environment. Where saline solution is used as the coupling fluid, the matching layer could be a hysol epoxy mixed with 3 µm alumina powder. Optionally, the space between the transducer elements 16 and 18 and the acoustic reflector 14 is filled with a solid material, e.g. a low loss fused silica, having suitable acoustic properties to ensure proper propagation of the acoustic beams 20 and 22.

Figure 3:
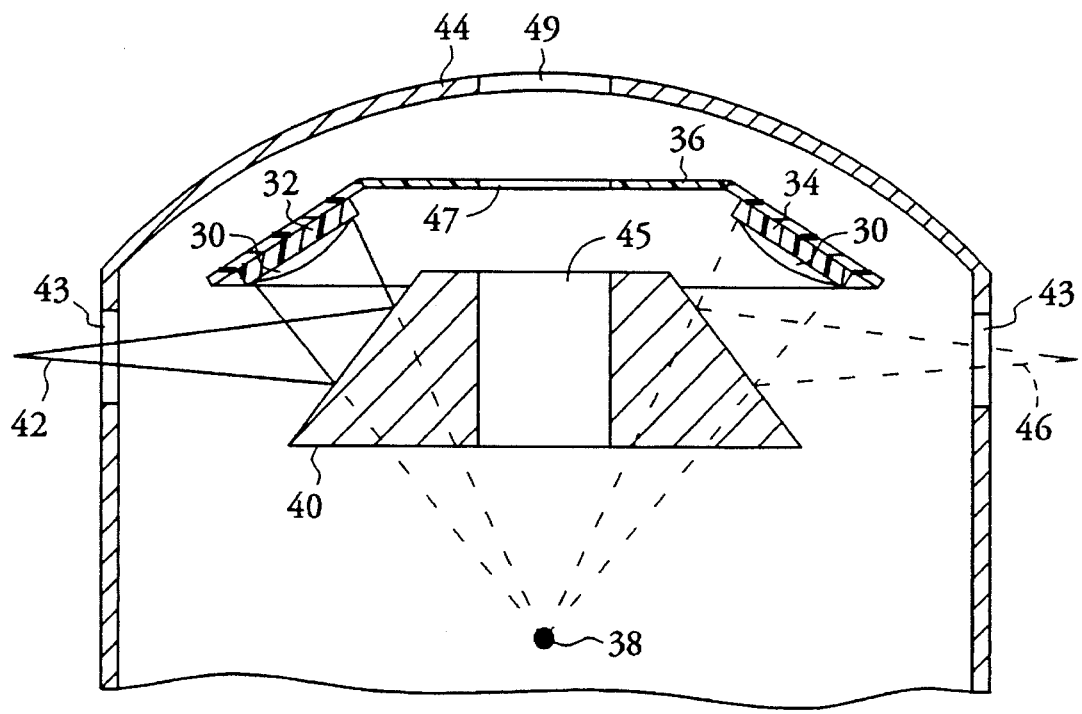
FIG. 3 is a schematic diametrical view of a second embodiment of the invention.

Referring now to FIG. 3, a second embodiment of the invention is shown as including a curvilinear cylindrical lens 30 at the radiating forward surfaces of piezoelectric transducer elements 32 and 34. The transducer elements are fixed to the interior surface of a frustroconically-shaped shell 36. Only two piezoelectric elements are shown, but the shell includes a full circle of elements. The curvilinear cylindrical lens extends over each of the transducer elements, but separate cylindrical lenses may also be used.

The cylindrical lens 30 improves the beam-forming characteristics of the array of transducer elements 32 and 34. The geometries of the shell 36 and the lens 30 define a focal point 38 for the individual acoustic beams from the transducer elements. Preferably, the focal point is along the coincident axes of the shell and an acoustic reflector 40. A-reference beam 42 is shown by solid lines. The focus of the reference beam is beyond the exterior of a probe housing 44. The cylindrical sidewall of the housing 44 includes an acoustic window 43 for passage of the interrogation beam and for passage of echo energy back into the housing. The acoustic window may be a polymer radome. The reflector 40 is shown as having a central hole 45 that is coincident with a hole 47 in the shell 36 and a hole 49 in the probe housing 44. These holes provide easy passage of a guide wire, according to standard medical practice. This type of arrangement may be used with any of the described and/or illustrated embodiments.

If the housing 44 is filled with a fluid, the transducer elements 32 and 34 can be moved relative to the reflector 40. For example, the shell may be fixed in position and the reflector 40 may be moved axially. While the focal length remains constant, the reference beam 42 that is reflected by the reflector 40 is moved axially. More importantly, the constant-focal length reference beam 42 will have a focal point that is displaced radially as the reflector is moved relative to the shell. Consequently, an interrogation beam has, in essence, a zone of focus.

From the direction of the reference beam 42, the subset of activated transducer elements is rotated or swung through 180° to form an interrogation beam 46. Continuing the rotation returns the interrogation beam to the reference direction 42.

Figure 4:
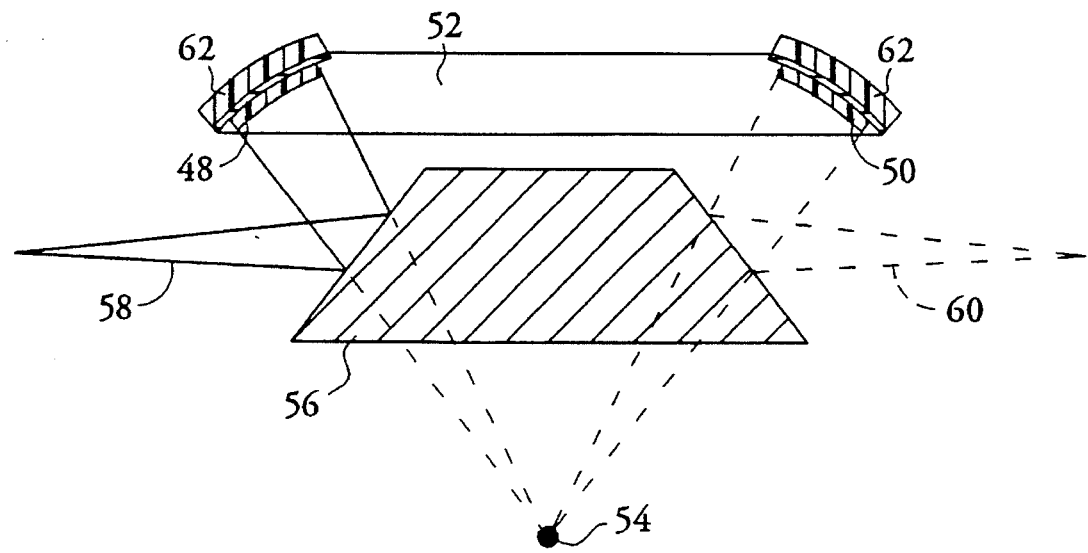
FIG. 4 is a schematic diametrical view of a third embodiment of the invention.

FIG. 4 illustrates an embodiment in which transducer elements 48 and 50 are formed on the inside surface of a truncated spherical shell 52. The shape of the shell contributes to the beam-forming characteristics of the device. In FIG. 4, the radius of the shell 52 provides a focus at a center 54. However, an acoustic reflector 56 deflects the acoustic energy from the transducer element 48 to provide a reference beam 58 shown in solid. The reference beam therefore has a focus, both in azimuth and elevation, that is determined by the curvature of the shell 52 and the distance of the reflector 56 from the transducer element 48. Because the shell 52 provides a means for focusing, a lens is not necessary.

An interrogation beam 60 is provided by sequencing the excitation of elements 48 and 50 180° from the subset utilized to form the original interrogation beam in the reference direction 58. Also shown in FIG. 4 is an acoustic absorber 62 at the rearward side of the truncated spherical shell 52. Excitation of the transducer elements generates acoustic energy in both the forward and rearward directions. The acoustic absorber minimizes the transmission of acoustic energy from the rearward surfaces of the elements to the surrounding environment. An acoustic absorber of proper design also provides a short, narrow interrogation pulse, capable of providing improved in-line resolution of targets.

Figure 5:
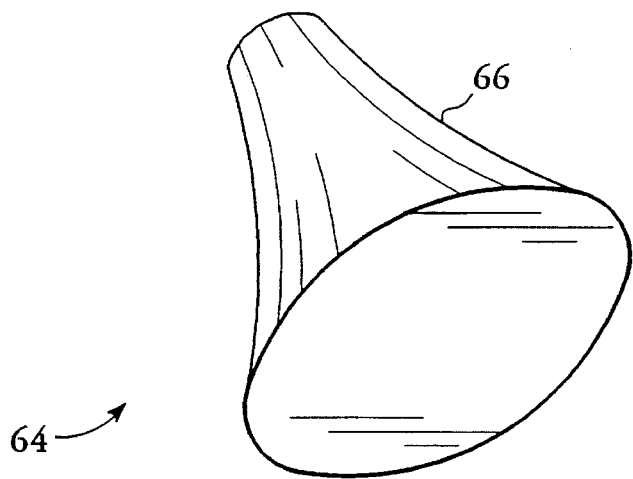
FIG. 5 is a perspective view of a second embodiment of the acoustic reflector of FIG. 1.

Referring now to FIG. 5, an acoustic reflector 64 is shown as having an outer surface 66 that contributes to the beam-forming characteristics of the acoustic probe into which the reflector is inserted. Rather than having a frustroconical shape, the reflector includes an outer surface that changes in slope with distance from virtual vertices of the reflector and a transducer-bearing shell of the type described above. The design of the outer surface contributes to the beam-forming characteristics of the ultrasonic probe. The outer surface presents a concave region to an individual transducer element in order to focus the acoustic beam generated from the element. Use of a convex outer surface is also contemplated.

Figure 6:
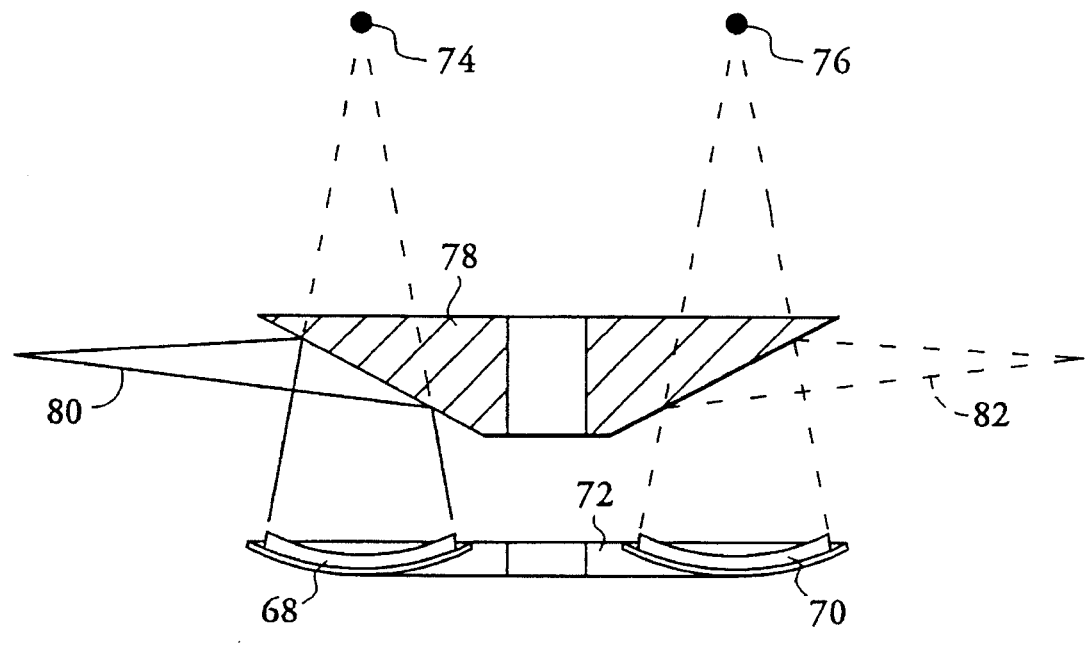
FIG. 6 is a schematic diametrical view of a fourth embodiment of the invention, with each transducer element in an array of elements directed to transmit acoustic energy in a direction parallel to the axis of the array.

In the embodiment of FIG. 6, transducer elements 68 and 70 are bonded to a shell 72 having a segmented toroidal configuration. Again, only two transducer elements are shown, but in practice a circular array is employed. The half-toroidal configuration positions the individual transducer elements to project acoustic energy in a direction substantially parallel to the axis of the shell 72. Virtual foci are spaced equidistantly from the shell, but reflector structure 78 redirects the acoustic beams, as represented by a reference beam 80 and a subsequent beam 82. Alternatively, a circular array of transducer elements may be formed on a flat surface, with one or more lens providing the focus. By changing the half angle of the reflector structure 78, look-forward and look-back ultrasonic probes may be formed.

Figure 7:
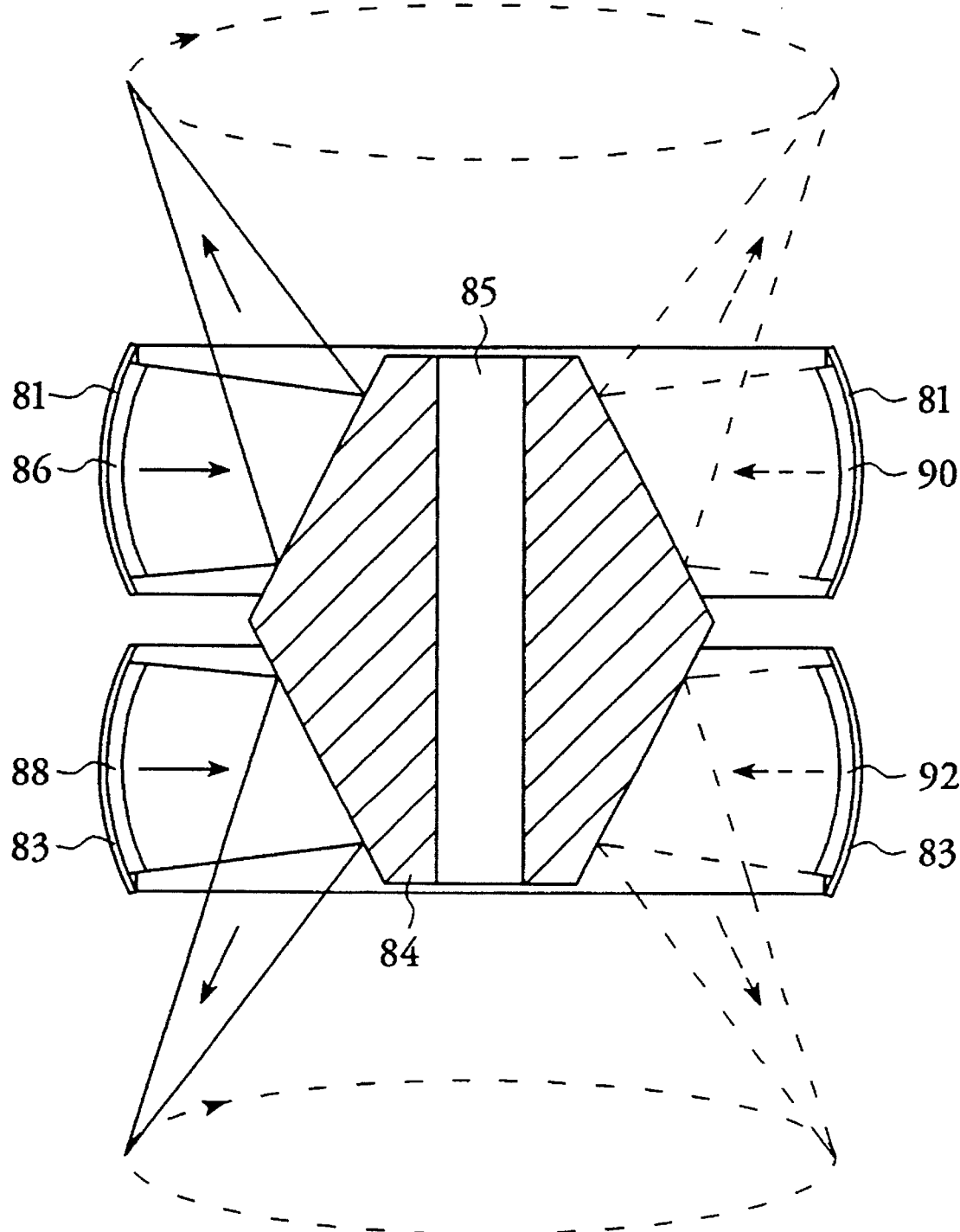
FIG. 7 is a schematic diametrical view of a fifth embodiment of the invention, with an array of transducer elements at opposed sides of an acoustic reflector.

In FIG. 7, two shells 81 and 83 are placed at opposite ends of a double sided reflector 84. The reflector is symmetrical to present conical surfaces to transducer elements 86, 88, 90 and 92 connected to the shells 72. The half angles of the conical configurations are such that both a look-forward view and a look-back view can be achieved when an ultrasonic probe containing the shells 72 and the reflector 84 is inserted in the direction of a central opening 85 that is provided for passage of an ultrasonic angioplasty device of the type used for recanalization of an occluded blood vessel. The transducer elements on shell 81 may be used to provide the look-forward view, while the transducer elements on shell 83 may provide the look-back view.

Figure 8:
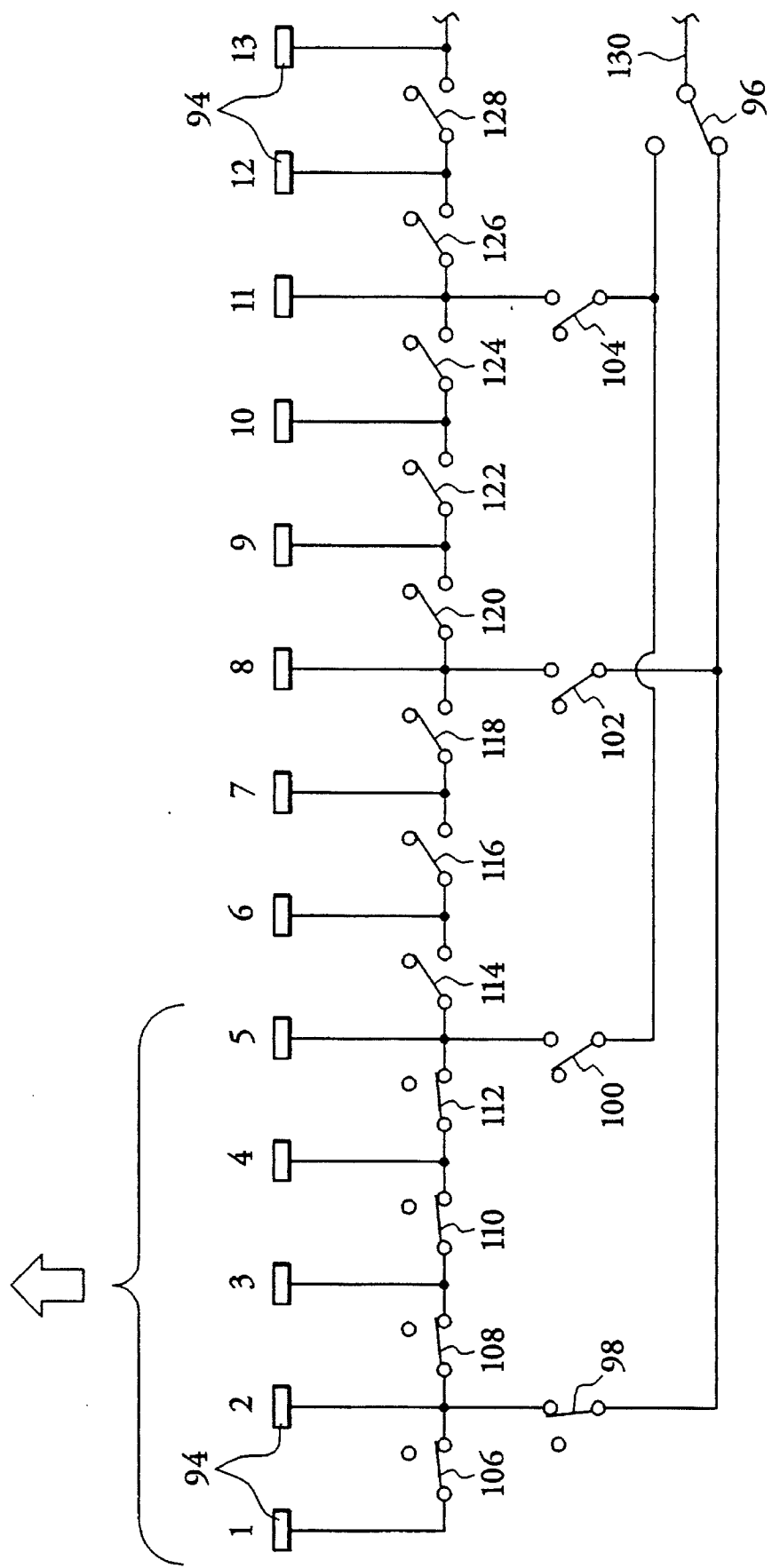
FIG. 8 is a schematic view of a multiplexer approach for selectively exciting transducer elements in an array of elements.

In FIG. 8, a multiplexing circuit for driving thirteen transducer elements 94 is shown as including a primary switch 96, four secondary switches 98, 100, 102 and 104 and a separate tertiary switch 106–128 for each of the transducer elements 94. An excitation signal is connected at an input line 130 to the primary switch 96. When the primary switch, the secondary switches and the tertiary switches are in the positions shown in FIG. 8, the first five transducer elements are electrically excited to collectively generate an interrogation beam. The five transducer elements are also employed to detect reflected energy from an object of interest. The interrogation beam is then progressed by opening tertiary switch 106 to deactivate the first transducer element and by closing tertiary switch 114 in order to activate the sixth transducer element. In a next step, the primary switch 96 is toggled, switches 98 and 108 are opened and switches 100 and 116 are closed, thereby isolating activations to the subset 3–7 of the transducer elements. Transducer elements 4–8 are activated by opening tertiary switch 110 and closing tertiary switch 118. In the next step, primary switch 96 is toggled, switches 110 and 112 are opened, and switches 102 and 120 are closed to activate elements 5–9. The interrogation beam can be systematically progressed in this manner. Typically, the multiplexing takes place within integrated circuitry at the probe level, so that a sixty-four element array does not require at least sixty-four separate wires from the probe to the imaging electronics.

Figure 9:
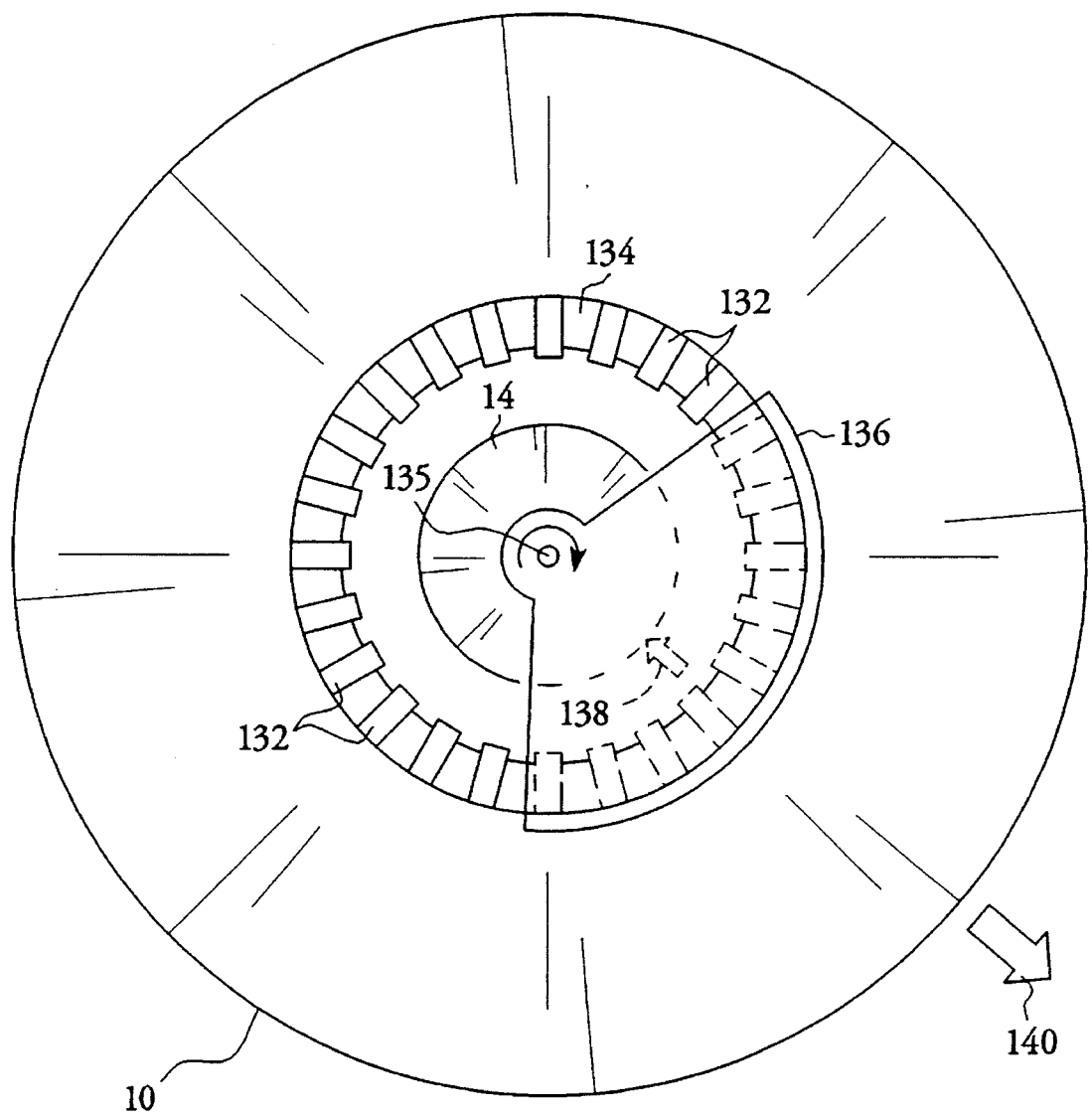
FIG. 9 is a top view of a second approach to activating subsets of transducer elements on the shell of FIG. 1.

As an alternative to the multiplexing approach of FIG. 8, FIG. 9 is a top view of a mechanical approach to progressively exciting subsets of transducer elements on the interior surface of the frustroconically-shaped shell 10 of FIG. 1. Electrodes 132 that are in one-to-one correspondence with transducer elements extend upwardly along the interior surface of the shell and bend over the top lip 134 of the shell. The electrodes 132 therefore have an inverted L-shaped configuration. Those portions that are bent over the lip 134 are exposed to a rotatable contact 136. The contact is a metallic member that is connected to a source of an excitation signal, not shown. The contact 136 is also connected to a drive shaft 135 for driving the contact about the axis of the shell 10.

The ten electrodes 132 that are physically and electrically connected to the contact 136 conduct the excitation signal to the operatively associated transducer elements. Consequently, a subset of the total number of transducer elements will generate acoustic energy in the direction of the reflector 14, as shown by arrow 138. Arrow 140 represents an interrogation beam that has been reflected by the reflector 14. The contact 136 may be rotated in a clockwise direction to sequentially disconnect the trail-end electrode and connect an electrode at the lead end of the contact. The rotation of the contact along the lip 134 of the shell 10 mechanically accomplishes the sequential triggering of transducer elements that is accomplished electrically in FIG. 8.

Returning to FIGS. 1 and 2, in operation a subset of transducer elements 12, 16 and 18 is triggered to transmit acoustic energy toward a central region having the acoustic reflector 14. The reflector is made of a material, such as stainless steel, that deflects the acoustic energy outwardly, as shown by arrows 24 and 26. Echo energy follows the reverse path to the subset of elements 12, 16 and 18. Because the acoustic path from the transducer elements has a component of direction that is inward, a greater number of elements can be activated at a particular time, as compared to emitting the acoustic energy outwardly. The beam characteristics of the ultrasonic probe can be tailored as desired by changing the geometry of the shell 10 or the reflector 14, or by providing a lens at the radiating surface of each transducer element.

I claim:

1. An ultrasonic probe comprising:

an array of ultrasonic transducer elements arranged axially about a central region having an axis, each transducer element having a forward surface facing the axis to define a first acoustic energy path toward said axis;

an acoustic reflector in spaced-apart relationship with said forward faces of said transducer elements, said acoustic reflector being positioned relative to said forward faces to be within said first acoustic paths and being configured to reflect said acoustic energy away from the axis along a second acoustic energy path different than said first acoustic paths; and electrode means connected to said transducer elements for sequentially electrically exciting said transducer elements, thereby initiating transmission of an acoustic signal along said first acoustic energy paths to scan radially around the axis.

2. The probe of claim 1 further comprising a housing having a window positioned within said second acoustic energy path, said array and said acoustic reflector being disposed in said housing such that said acoustic reflector is aligned to reflect acoustic energy between said transducer elements and said window.

3. The probe of claim 1 wherein said array is a curvilinear array of transducer elements.

4. The probe of claim 1 further comprising triggering means for transmitting excitation signals to selected transducer elements of said array via said electrode means.

5. The probe of claim 1 wherein said acoustic reflector has an axis coincident with the axis of said array of transducer elements and has an increasing cross-sectional diameter along said axis of said reflector, said acoustic reflector being dimensioned to define said second acoustic energy path as being perpendicular to said axes.

6. The probe of claim 1 wherein said acoustic reflector has an axis coincident with the axis of said array of transducer elements and has an increasing cross-sectional diameter along said axis of said reflector, said acoustic reflector being dimensioned to reflect an acoustic beam in a direction between said axes and the normal to said axes.

7. The probe of claim 1 further comprising cylindrical lens means for focusing acoustic energy emitted by said transducer elements.

8. The probe of claim 1 wherein said transducer elements are fixed to a curved interior surface of a shell.

9. The probe of claim 1 wherein said electrode means includes a first electrode for each of said transducer elements, said probe further comprising means for electrically connecting a selected number of adjacent first electrodes, said means for electrically connecting being displaceable to vary the electrically connected first electrodes.

10. The probe of claim 1 wherein said acoustic reflector has a geometry which contributes to focusing acoustic energy.

11. The probe of claim 1 further comprising a housing having a longitudinal axis and a window transparent to acoustic energy such that the probe is adapted for imaging an object's interior.

12. The probe of claim 1 wherein the transducer elements are arranged in less than 360° about the central region.

13. An ultrasonic catheter for imaging an interior of an object of interest comprising:

a catheter housing having a window substantially transparent to passage of acoustic energy, and said catheter housing having a longitudinal axis;

transducer means for transmitting acoustic waves from said catheter housing via said window and for sensing acoustic waves entering said catheter housing via said window, said transducer means including a plurality of fixed piezoelectric elements arranged axially about a central region about the axis and a fixed acoustic reflector, said piezoelectric elements having radiating surfaces facing generally toward said longitudinal axis and toward said acoustic reflector, said acoustic reflector having a geometry and being aligned to deflect acoustic waves from said radiating surfaces through said window of said catheter housing.

14. The catheter of claim 13 wherein said piezoelectric elements are fixed along a curved surface having an axis coincident with said longitudinal axis.

15. The catheter of claim 13 wherein said radiating surfaces are at approximately the same angle to said longitudinal axis.

16. The catheter of claim 15 wherein said acoustic reflector has a diameter that varies along said longitudinal axis, with each cross section perpendicular to said longitudinal axis being disk-shaped.

17. The catheter of claim 16 wherein said acoustic reflector has a frustroconical configuration.

18. An ultrasonic catheter for imaging an interior of an object of interest comprising:

a housing having a longitudinal axis and a window transparent to acoustic energy;

an array of transducer elements disposed symmetrically axially about a central region about said longitudinal axis within said housing, each transducer element directed to transmit acoustic energy along a path misaligned with said window;

an acoustic reflector positioned to deflect acoustic energy between said window and said transducer elements, said acoustic reflector having a surface that defines a slope to said longitudinal axis; and electrode means to selectively excite said transducer elements.

19. The catheter of claim 18 wherein electrode means includes first electrodes that are L-shaped and are selectively connected to a source of an excitation signal by a contact aligned to connect a portion of said first electrodes, said contact being rotatably mounted within said housing.

20. The catheter of claim 18 wherein said array of transducer elements is fixed to a surface having a hollowed toroidal configuration.

21. The catheter of claim 18 wherein said acoustic reflector is a metallic member having a frustroconical shape.

22. An ultrasonic probe for travel along an axis comprising:

a first array of ultrasonic transducer elements arranged axially about a first central region having an axis;

a second array of ultrasonic transducer elements arranged axially about a second central region different from said first central region, the first and the second central regions having the same axis; and reflector means for redirecting acoustic energy from said first array in a look-forward direction with respect to said travel and for redirecting acoustic energy from said second array in a look-back direction with respect to said travel to scan radially around the central regions, said first and second arrays and said reflector means being arranged to permit passage of one of a guide member and angioplasty device.

23. An ultrasonic probe comprising:

an array of ultrasonic transducer elements arranged about a central region, each transducer element having a forward surface directed to define a first acoustic energy path having a component of direction that is toward said central region;

an acoustic reflector in spaced-apart relationship with said forward faces of said transducer elements, said acoustic reflector being positioned relative to said forward faces to be within said first acoustic paths and being configured to reflect said acoustic energy along a second acoustic energy path different than said first; and electrode means connected to said transducer elements for electrically exciting said transducer elements, thereby initiating transmission of an acoustic signal along said first acoustic energy paths;

wherein said transducer elements are arranged in a truncated conical configuration.

* * * * *